United States Patent
Toth

(10) Patent No.: US 7,688,936 B2
(45) Date of Patent: Mar. 30, 2010

(54) METHOD AND APPARATUS OF MULTI-ENERGY IMAGING

(75) Inventor: Thomas L. Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 838 days.

(21) Appl. No.: 11/465,947

(22) Filed: Aug. 21, 2006

(65) Prior Publication Data
US 2007/0078336 A1    Apr. 5, 2007

Related U.S. Application Data

(63) Continuation of application No. 10/063,366, filed on Apr. 16, 2002.

(51) Int. Cl.
*A61B 6/00*    (2006.01)

(52) U.S. Cl. .................. 378/5; 378/4; 378/16; 378/101; 378/105; 378/145; 378/156; 378/158; 600/425; 600/427

(58) Field of Classification Search ...................... 378/4, 378/5, 16, 19, 101, 156, 207, 145, 158; 382/128, 382/130, 131; 600/425, 427
See application file for complete search history.

(56) References Cited

U.S. PATENT DOCUMENTS

| | | | | |
|---|---|---|---|---|
| 4,017,192 A | | 4/1977 | Rosenthal | |
| 4,307,726 A | * | 12/1981 | Paulson et al. | 600/407 |
| 4,562,540 A | * | 12/1985 | Devaney | 700/90 |
| 4,598,366 A | * | 7/1986 | Devaney | 700/90 |
| 4,686,695 A | * | 8/1987 | Macovski | 378/146 |
| 4,780,897 A | | 10/1988 | McDaniel et al. | |
| 4,975,933 A | | 12/1990 | Hampel | |
| 5,081,660 A | * | 1/1992 | Fujisaki | 378/156 |
| 5,262,946 A | | 11/1993 | Heuscher | |
| 5,485,492 A | * | 1/1996 | Pelc | 378/5 |
| 5,661,774 A | * | 8/1997 | Gordon et al. | 378/101 |
| 5,747,812 A | * | 5/1998 | DiFilippo | 250/363.1 |
| 5,917,877 A | * | 6/1999 | Chiabrera et al. | 378/207 |
| 6,081,322 A | * | 6/2000 | Barbour | 356/73.1 |
| 6,226,352 B1 | * | 5/2001 | Salb | 378/98.9 |
| 6,236,709 B1 | | 5/2001 | Perry et al. | |
| 6,950,492 B2 | * | 9/2005 | Besson | 378/5 |
| 6,973,158 B2 | * | 12/2005 | Besson | 378/16 |
| 7,158,611 B2 | * | 1/2007 | Heismann et al. | 378/98.9 |

(Continued)

OTHER PUBLICATIONS

Kelcz, F., Joseph, P., Hilal, S., Noise considerations in dual energy CT scanning, Med. Phys. 6(5), Sep./Oct. 1979, p. 418-425.

*Primary Examiner*—Brian Casler
*Assistant Examiner*—Baisakhi Roy
(74) *Attorney, Agent, or Firm*—Ziolkowski Patent Solutions Group, SC

(57) ABSTRACT

The present invention is directed to a method and apparatus of multi-energy data acquisition. An imaging system is also provided and includes a number of HF electromagnetic energy filters. The filters include at least a first and a second filter wherein the first filter is positioned in a path of HF electromagnetic energy when an HF electromagnetic energy source is energized to a first voltage and the second filter is positioned in the path of HF electromagnetic energy when the HF electromagnetic energy source is energized to a second voltage.

25 Claims, 6 Drawing Sheets

U.S. PATENT DOCUMENTS

2003/0195416 A1\* 10/2003 Toth .......................... 600/427
2004/0264626 A1\* 12/2004 Besson ........................ 378/4
2006/0280282 A1\* 12/2006 Toth ............................. 378/5
2007/0078336 A1\* 4/2007 Toth .......................... 600/425

\* cited by examiner

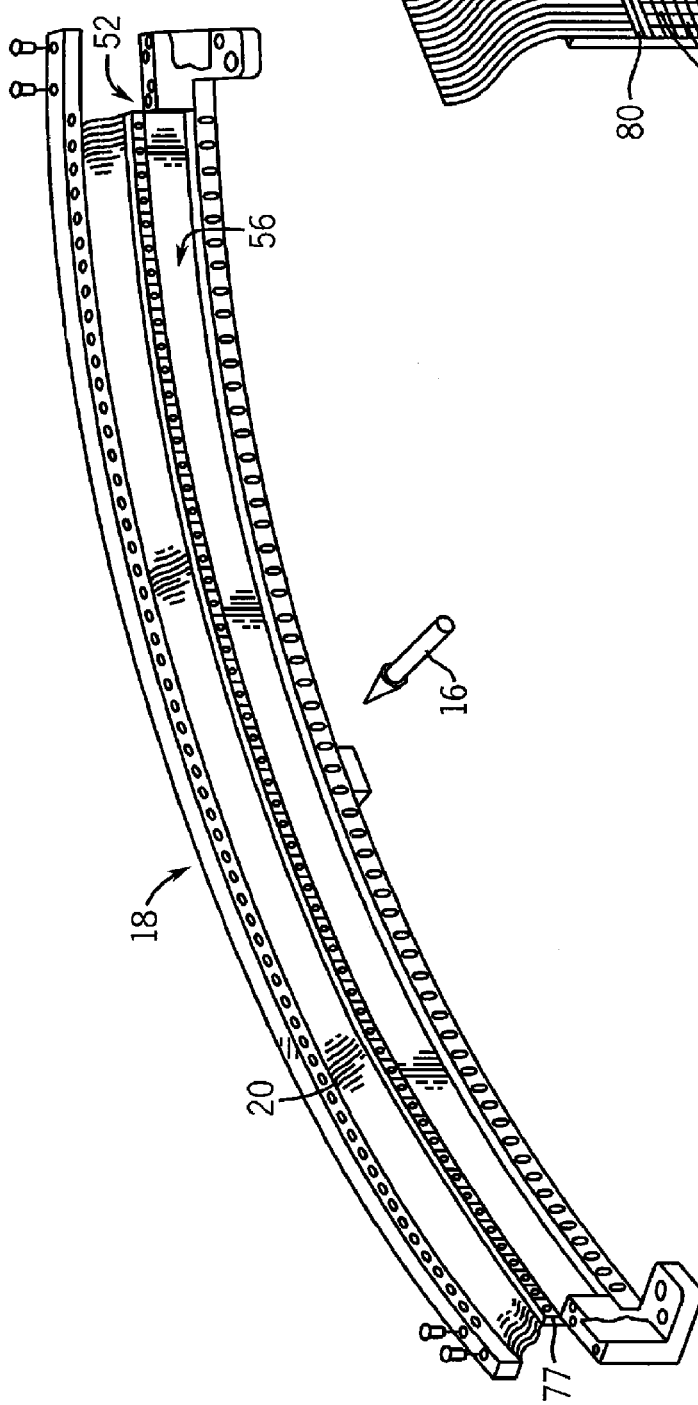
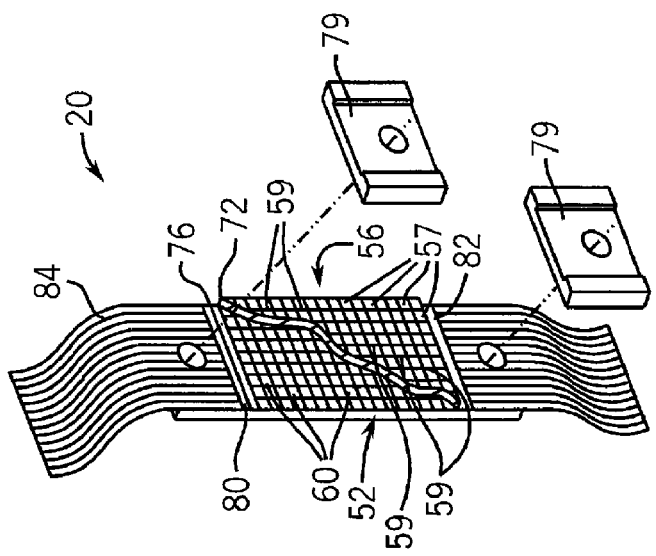
FIG. 3
FIG. 4

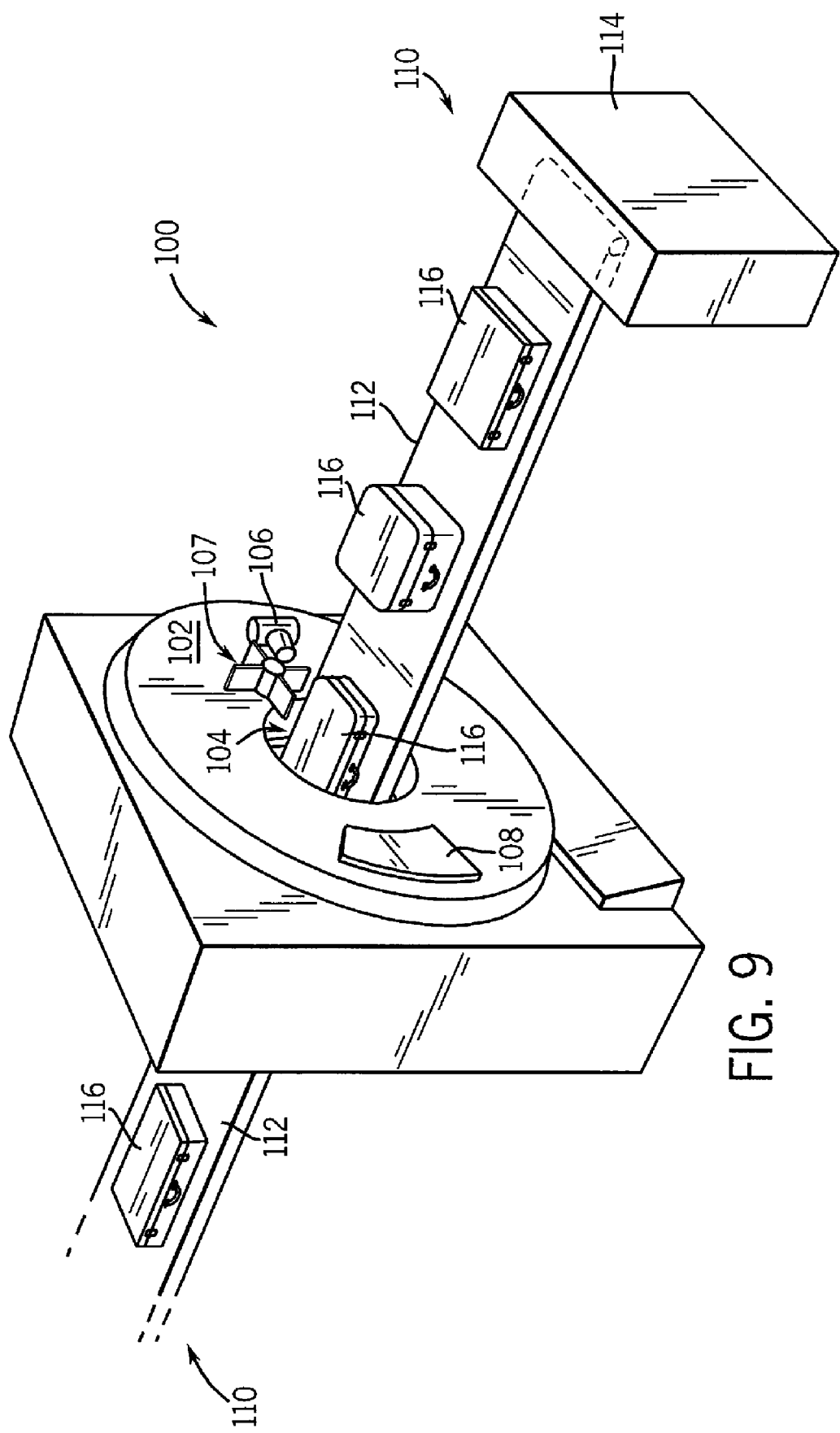

METHOD AND APPARATUS OF MULTI-ENERGY IMAGING

CROSS REFERENCE TO RELATED APPLICATIONS

The present application is a continuation of and claims priority of U.S. Ser. No. 10/063,366 filed Apr. 16, 2002, the disclosure of which is incorporated herein by reference.

BACKGROUND OF THE INVENTION

The present invention relates generally to diagnostic imaging and, more particularly, to a method and apparatus of acquiring imaging data at more than one energy range using multi-energy high speed switching filters.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Recently, dual energy CT scanning commonly referred to as "tomochemistry" has increasingly been used as a means of gaining diagnostic information of a subject. A principle objective of dual energy scanning is to obtain diagnostic CT images that enhance contrast separation within the image by utilizing two scans at different chromatic energy states. A number of techniques have been proposed to achieve dual energy scanning including a "Two Crystal" method and a "Two kV" method. These two techniques were discussed by F. Kelcz, et al. in an article in Medical Physics 6(5), SEP./OCT. (1979) entitled "Noise Considerations in Dual Energy CT Scanning." With respect to the "Two kV" technique, high frequency generators have made it possible to switch the kVp potential of the high frequency electromagnetic energy projection source on alternating views. As a result, data for two dual energy images may be obtained in a temporarily interleaved fashion rather than two separate scans made several seconds apart as required with previous CT technology. Simply scanning at two kVp potentials in an interleaved manner is not desirable as filtration of the dual energy levels remains a concern. For example, dual energy CT scanning with fixed filtration results in a dramatic decrease in signal strength when comparing the 80 kVp spectrum to the 140 kVp spectrum. Furthermore, the effective energy separation between the two spectrums is approximately 25 kV. Selectively filtering each kVp spectrum with different x-ray filtration can increase the energy separation to 45 kV in this case. This dramatically improves the effectiveness of dual energy CT imaging.

Therefore, it would be desirable to design an apparatus and method for acquiring imaging data at more than one energy state during a single scan without jeopardizing signal strength.

BRIEF DESCRIPTION OF THE INVENTION

The present invention is directed to a method and apparatus of multi-energy imaging overcoming the aforementioned drawbacks. A set of rotatable filters is provided and controlled by a controller configured to position each filter in a path of high frequency electromagnetic energy synchronously with a changing kVp cycle. By using a pulsed high frequency electromagnetic energy source together with the set of filters, a burst of high frequency electromagnetic energy beams may be generated at a desired energy/filtration combination for each view. A set of views properly filtered for the high frequency electromagnetic energy implemented may then be generated and used for image reconstruction.

Therefore, in accordance with one aspect of the present invention, a CT system comprises a rotatable gantry having an opening for receiving a subject to be scanned. The CT system further includes a high frequency electromagnetic energy source configured to project a number of high frequency electromagnetic energy beams towards the subject. A generator is also provided and configured to energize the high frequency electromagnetic energy source to at least a first energy state and a second energy state. The CT system also includes a number of high frequency electromagnetic energy filters positionable between the high frequency electromagnetic energy source and the subject. The number of high frequency electromagnetic energy filters includes at least a first filter and a second filter wherein the first filter is positioned between the high frequency electromagnetic energy source and the subject when the high frequency electromagnetic energy source is energized to the first energy state. The second filter is configured to be positioned between the high frequency electromagnetic energy source and the subject when the high frequency electromagnetic energy source is energized to the second energy state.

In accordance with a further aspect of the present invention, a controller is configured to acquire CT imaging data at more than one chromatic energy state. The controller has instructions to energize a high frequency electromagnetic energy source configured to project a high frequency electromagnetic energy beam toward a subject to be scanned to a first voltage potential. The controller has further instructions to position a first portion of a filtering apparatus between the subject and the high frequency electromagnetic energy source along a path of rotation during energization of the high frequency electromagnetic energy source to the first voltage potential. The controller also has instructions to energize the high frequency electromagnetic energy source to a second voltage potential. The controller is then instructed to position a second portion of the filtering apparatus between the subject and the high frequency electromagnetic energy source along the path of rotation during energization of the high frequency electromagnetic energy source to the second voltage potential.

In accordance with a further aspect of the present invention, a method of acquiring imaging data at more than one chromatic energy comprises the step of projecting a first beam of electromagnetic energy along a projection path toward a subject. The method further includes the step of positioning a first filter in the projection path during projection of the first beam. The method also includes projecting a second beam of electromagnetic energy along the projection path toward the subject and positioning a second filter in the projection path during projection of the second beam of electromagnetic energy.

In accordance with yet a further aspect of the present invention, a computer readable storage medium has a computer program stored thereon. The computer program represents a set of instructions that when executed by a computer causes the computer to energize the high frequency electromagnetic energy source to a first voltage to cause the high frequency electromagnetic energy source to project a first beam of electromagnetic energy toward the subject to be scanned. The computer is further caused to position a first filter between the high frequency electromagnetic energy source and the subject during energization of the high frequency electromagnetic energy source to the first voltage. The set of instructions further causes the computer to energize the high frequency electromagnetic energy source to a second voltage to cause the high frequency electromagnetic energy source to project a second beam of electromagnetic energy toward the subject and position a second filter between the electromagnetic energy source and the subject during energization of the high frequency electromagnetic energy source to the second voltage.

In accordance with yet another aspect of the present invention, a filtering apparatus for a radiation emitting imaging system is provided. The filtering apparatus includes a hub having a number of connection ports and a first filter connected to the hub at a first connection port and a second filter connected to the hub at a second connection port. The first filter is configured to have a first filtering power and the second filter is configured to have a second filtering power.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

FIG. 9 is a pictorial view of a CT system for use with a non-invasive package inspection system.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate, that the present invention is equally applicable for the detection and conversion of other high frequency electromagnetic energy. The present invention will be described with respect to a "third generation" CT scanner, but is equivalently applicable with other CT systems.

Figure 1:
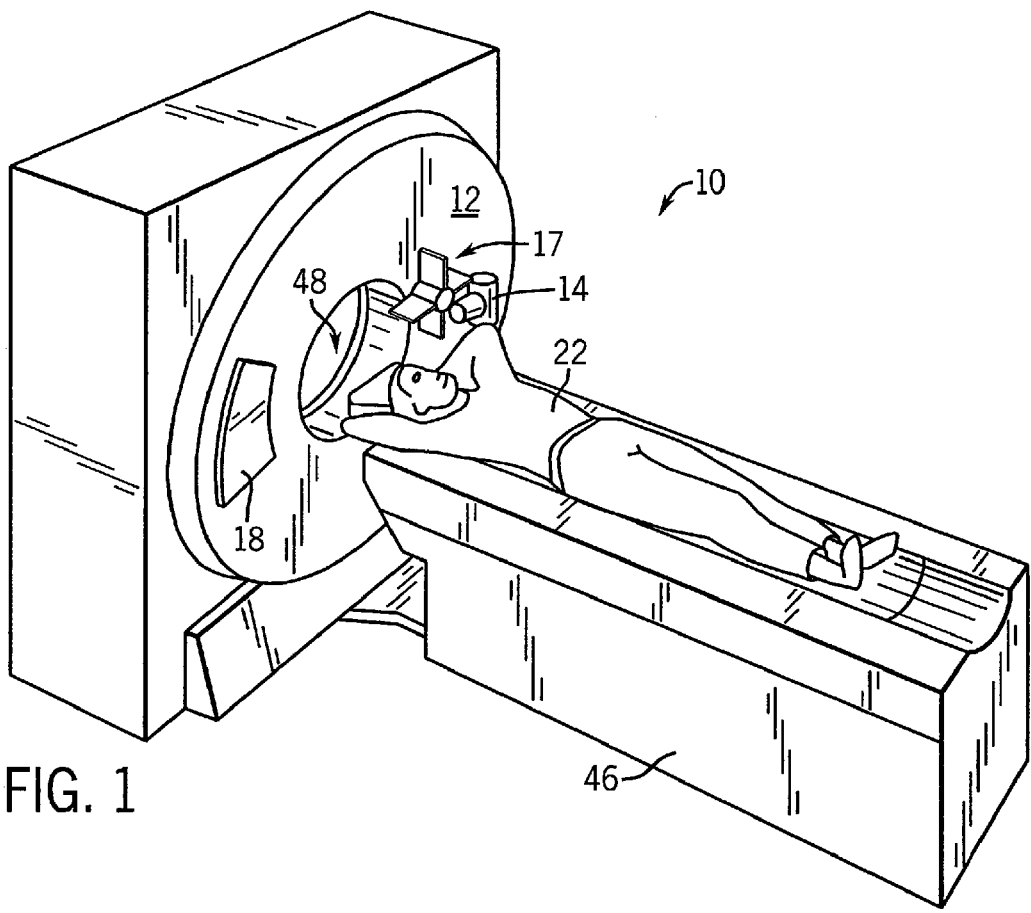
FIG. 1 is a pictorial view of a CT imaging system.
Figure 2:
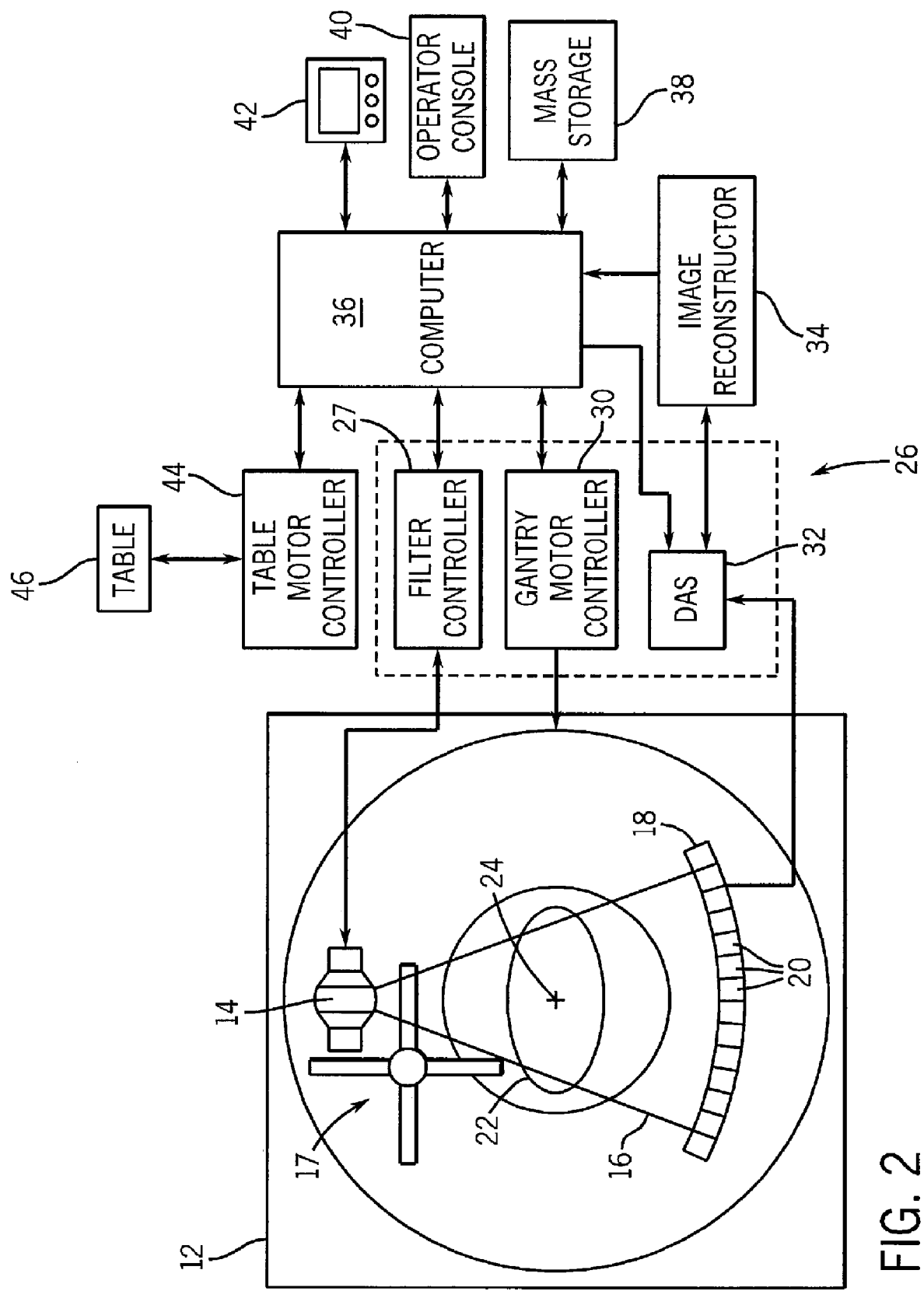
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a filtering apparatus 17 and a detector array 18 on the opposite side of the gantry 12. The filtering apparatus 17 may include a pre-patient filter, a post-patient filter, or both. In FIGS. 1 and 2, the filtering apparatus 17 is shown as a pre-patient filter, as will be described more fully with respect to FIGS. 6-8. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon including source 14, filtering apparatus 17, and detector array 18 rotate about a center of rotation 24.

Rotation of gantry 12 and the operation of x-ray source 14 are governed by a control mechanism 26 of CT system 10. As will be described below, control mechanism 26 includes a filter controller 27 that provides positioning signals to filtering apparatus 17. Control mechanism 26 also includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard or other data entry module. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of photodiodes 60 forming a photodiode array 52 and a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector material 59 is interstitially disposed between each scintillator 57 to reduce light spreading from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
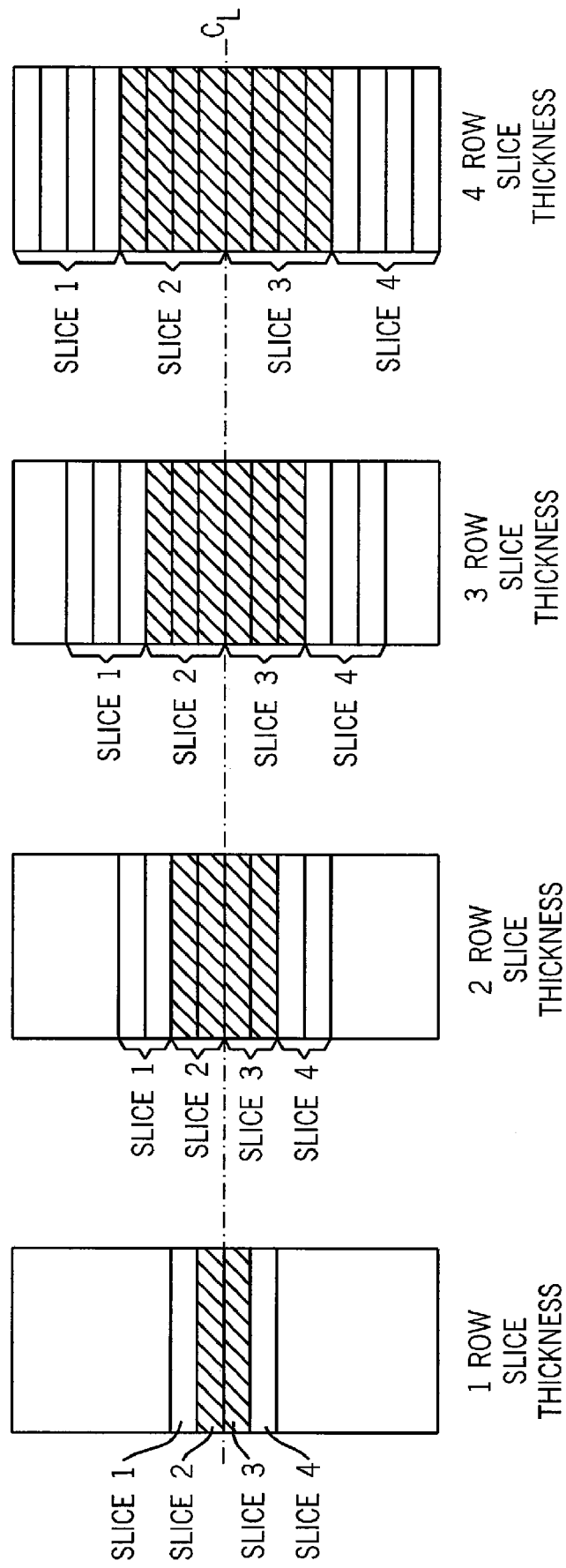
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
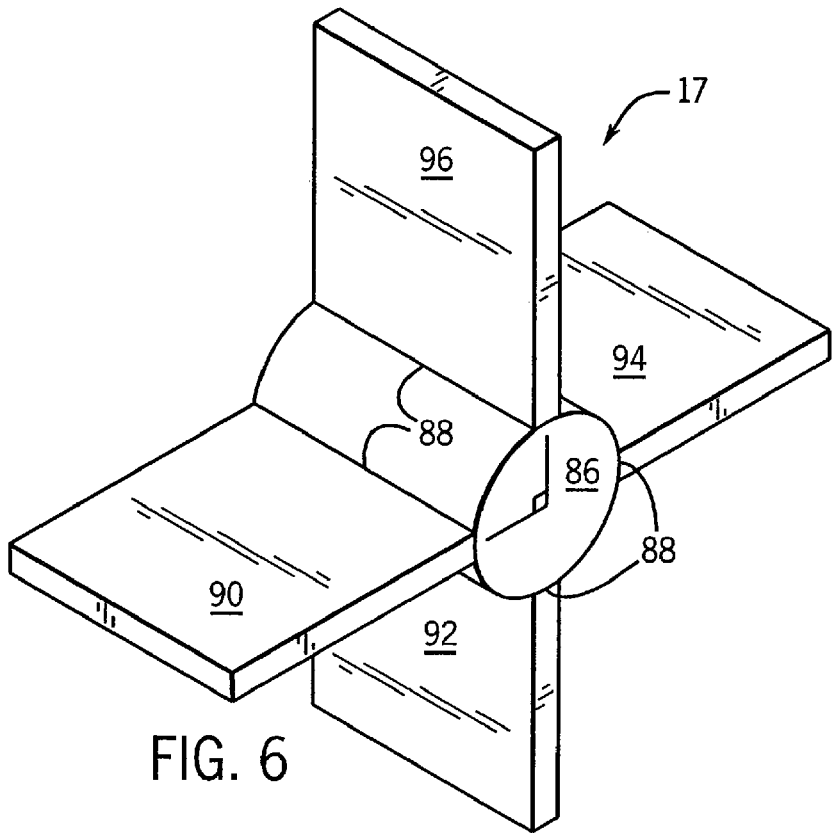
FIG. 6 is a perspective view of one embodiment of a filtering apparatus in accordance with the present invention.

Referring now to FIG. 6, a four-spoked filtering apparatus 17 is shown. While a four-spoked filtering apparatus will be described, the present invention is not so limiting and therefore a filtering apparatus with less than four filter spokes as well as a filtering apparatus with more than four filter spokes are contemplated and within the scope of the present invention. Filtering apparatus 17 includes a hub 86 having a number of connection ports 88. In this embodiment, a connection port 88 is positioned every 90° around the hub. Hub 86 is shown as a cylinder but a spherical hub is also contemplated. In a three-spoked filtering apparatus, each connection port would be located every 120° along the hub. Connected to hub 86 at each connection port 88 is a filter 90. Each filter member 90 may be connected to hub 86 at connection port 88 in a number of known manners. For example, filtering member 92-96 may be snap-fit, bolted, or integrated with hub 86 as a single integral body. In this embodiment, each connection port 86 includes a slot for receiving a filter but other receiving designs are contemplated. As will be described below, each filtering member 92-96 has a differing filtering power. That is, filtering member 90 has a filtering power different from the filtering power of filter 94 and so forth.

Hub 86 includes circuitry (not shown) that responds to electrical signals generated by filter controller 27, FIG. 2, to position one of the filters 90-96 in a path of high frequency electromagnetic energy. Hub 86 is thereby caused to rotate filters 90-96 into the high frequency electromagnetic energy path synchronously with energization of the high frequency electromagnetic energy projection source 14 of FIG. 1. The synchronous relationship of filter position and source energization is best shown in FIG. 7.

Figure 7:
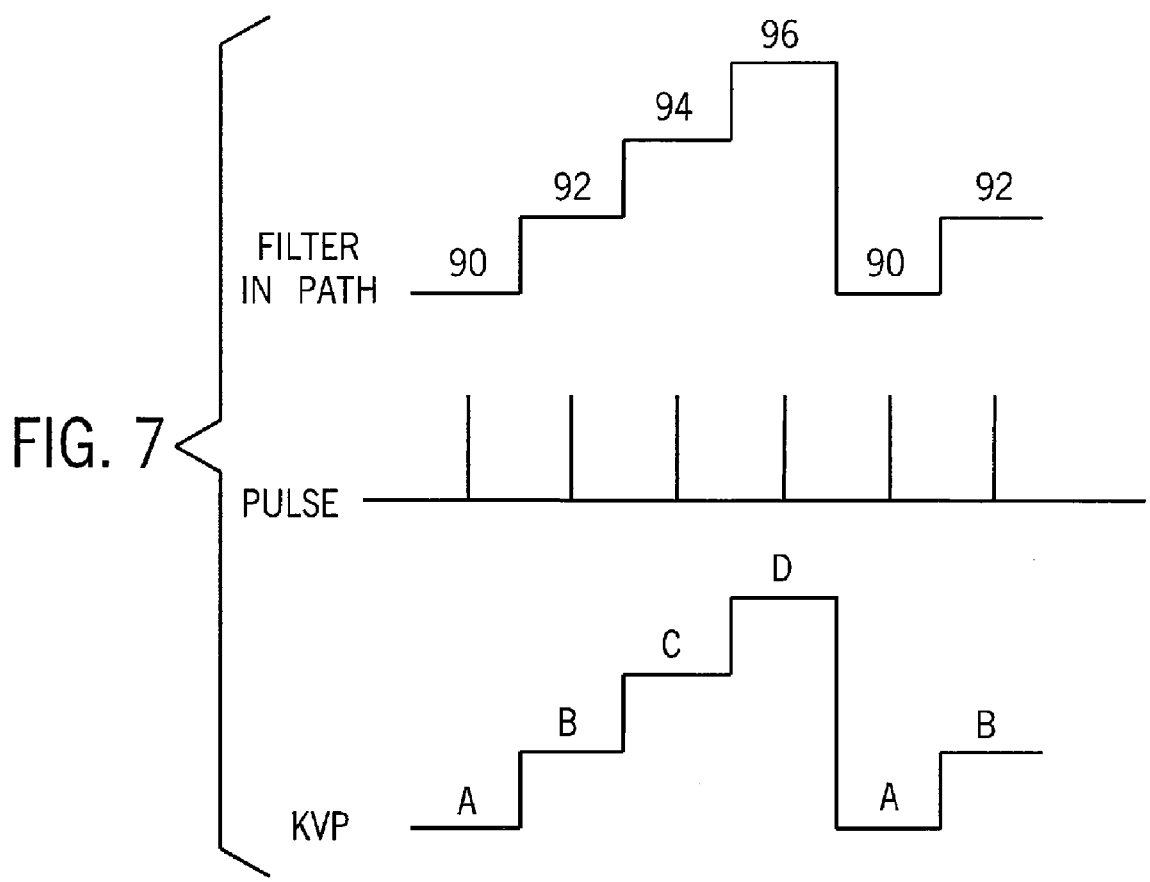
FIG. 7 illustrates positioning of each filter of the filtering apparatus as a function of energy applied to a high frequency electromagnetic energy projection source.

Shown in FIG. 7 are three plots illustrating the position of each filter with respect to the kVp potential of the high frequency electromagnetic energy source. As shown, a first filter, such as filter 90, is positioned in the path of high frequency electromagnetic energy when the high frequency electromagnetic energy source projects a burst of high frequency electromagnetic energy having a kVp potential A. The x-ray source then emits a second burst of x-rays having a kVp potential B and simultaneously therewith filter 92 is positioned in the x-ray path. Thereafter, the x-ray source emits another burst of x-rays having a kVp potential C. Simultaneously therewith, filter 94 is rotated by the hub into the x-ray path. The x-ray source is then instructed to emit another burst of x-rays having a kVp potential D. When the x-ray source generates the burst of x-rays at potential D, the filter controller transmits a signal to the filtering apparatus to position filter 96 in the x-ray path.

FIG. 7 illustrates the positioning of each filter in the x-ray path depending upon the kVp potential of the beam of x-rays. However, the present invention does not require the sequential placement of each filter as described above. That is, depending upon the requirements of the imaging protocol filter 96 may be positioned in the x-ray path after filter 90. Ultimately, the order by which the filters are positioned in the x-ray path is not limited to the sequential description provided above.

Figure 8:
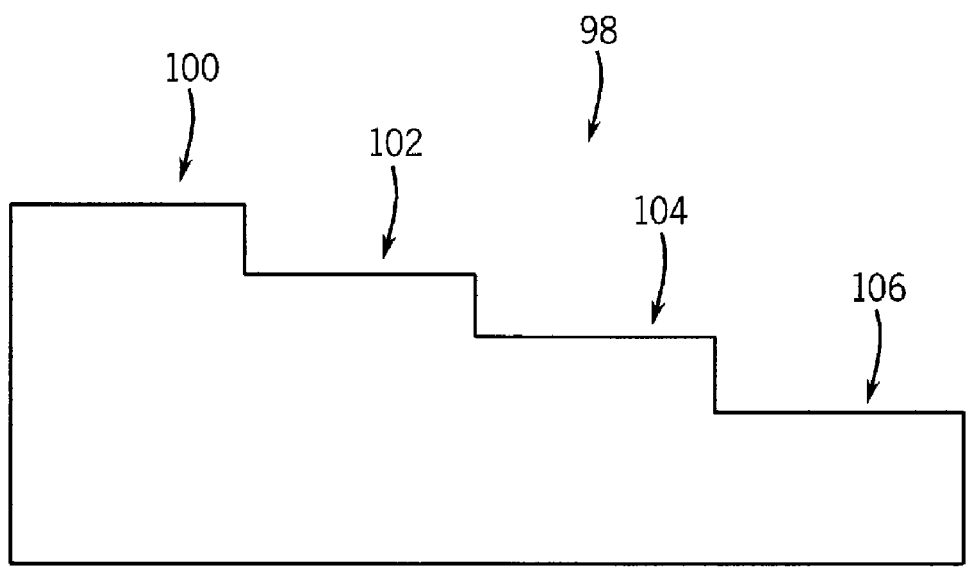
FIG. 8 is a cross-sectional view of an alternate embodiment of a filtering apparatus in accordance with the present invention.

Referring now to FIG. 8, a filtering apparatus 98 in accordance with another embodiment of the present invention is shown. Filtering apparatus 98 may be used with or independently of filtering apparatus 17 specifically described in FIG. 6. In the illustrated embodiment, filtering apparatus 98 includes a single filter comprising a number of filtering sections 100-106. Each filtering section 100-106 has a different filtering power. Therefore, filtering apparatus 98 may be used for multi-energy CT scanning. Filtering apparatus 98 is designed such that one section 100-106 is positioned in the x-ray path depending upon the kVp potential of the x-ray beam. For example, when the x-ray beam has a high kVp potential filtering section 100 may be positioned in the x-ray path. Whereas, when the x-ray beam has a lower kVp potential filtering section 106 is positioned within the x-ray path. Filtering apparatus 98 is shown as comprising four separate and distinct filtering sections. However, the present invention is not limited to only four sections and therefore a filtering apparatus with less than four sections or more than four sections is equivalently applicable with the present invention.

In an alternate embodiment of the present invention, the filtering apparatus 98 shown in FIG. 8 is incorporated with the four-spoked filtering apparatus 17 illustrated in FIG. 6. With this embodiment, each filter 90-96 has a number of filtering sections similar to that shown in FIG. 8. As a result, the number of filtering combinations can be increased without requiring multiple filtering apparatuses. For example, in a four-spoked filtering apparatus wherein each filter has four filtering sections, a total of sixteen filtering combinations may be utilized in acquiring imaging data.

Referring now to FIG. 9, package/baggage inspection system 100 includes a rotatable gantry 102 having an opening 104 therein through which packages or pieces of baggage may pass. The rotatable gantry 102 houses a high frequency electromagnetic energy source 106 and a filtering apparatus 107, as well as a detector assembly 108. Filtering apparatus 107 is shown as being positioned between the source 106 and object 116. However, filtering apparatus 107 could be placed between object 116 and detector assembly 108. In another embodiment, a first filter is positioned pre-object and a second filter positioned post-object. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc. by viewing the images on a display (not shown).

Therefore, in accordance with one embodiment of the present invention, a CT system comprises a rotatable gantry having an opening for receiving a subject to be scanned. The CT system further includes a high frequency electromagnetic energy source configured to project a number of high frequency electromagnetic energy beams towards the subject. A generator is also provided and configured to energize the high frequency electromagnetic energy source to at least a first energy state and a second energy state. The CT system also includes a number of high frequency electromagnetic energy filters positionable between the high frequency electromagnetic energy source and the subject. The number of high frequency electromagnetic energy filters includes at least a first filter and a second filter wherein the first filter is positioned between the high frequency electromagnetic energy source and the subject when the high frequency electromagnetic energy source is energized to the first energy state. The second filter is configured to be positioned between the high frequency electromagnetic energy source and the subject when the high frequency electromagnetic energy source is energized to the second energy state.

In accordance with a further embodiment of the present invention, a controller is configured to acquire CT imaging data in more than one chromatic energy state. The controller has instructions to energize a high frequency electromagnetic energy source configured to project a high frequency electromagnetic energy beam toward a subject to be scanned to a first voltage potential. The controller has further instructions to position a first portion of a filtering apparatus between the subject and the high frequency electromagnetic energy source along a path of rotation during energization of the high frequency electromagnetic energy source to the first voltage potential. The controller also has instructions to energize the high frequency electromagnetic energy source to a second voltage potential. The controller is then instructed to position a second portion of the filtering apparatus between the subject and the high frequency electromagnetic energy source along the path of rotation during energization of the high frequency electromagnetic energy source to the second voltage potential.

In accordance with a further embodiment of the present invention, a method of acquiring imaging data at more than one chromatic energy comprises the step of projecting a first beam of electromagnetic energy along a projection path toward a subject. The method further includes the step of positioning a first filter in the projection path during projection of the first beam. The method also includes projecting a second beam of electromagnetic energy along the projection path toward the subject and includes the step of positioning a second filter in the projection path during projection of the second beam of electromagnetic energy.

In accordance with yet a further embodiment of the present invention, a computer readable storage medium has a computer program stored thereon. The computer program represents a set of instructions that when executed by a computer causes the computer to energize high frequency electromagnetic energy source to a first voltage to cause the high frequency electromagnetic energy source to project a first beam of electromagnetic energy toward the subject to be scanned. The computer is further caused to position a first filter between the high frequency electromagnetic energy source and the subject during energization of the high frequency electromagnetic energy source to the first voltage. The set of instructions further causes the computer to energize the high frequency electromagnetic energy source to a second voltage to cause the high frequency electromagnetic energy source to project a second beam of electromagnetic energy toward the subject and position a second filter between the electromagnetic energy source and the subject during energization of the high frequency electromagnetic energy source to the second voltage.

In accordance with yet another embodiment of the present invention, a filtering apparatus for a radiation emitting imaging system is provided. The filtering apparatus includes a hub having a number of connection ports and a first filter connected to the hub at a first connection port and a second filter connected to the hub at a second connection port. The first filter is configured to have a first filtering power and the second filter is configured to have a second filtering power.

The present invention has been described in terms of the preferred embodiment, and it is recognized that equivalents, alternatives, and modifications, aside from those expressly stated, are possible and within the scope of the appending claims.

What is claimed is:

1. A CT system comprising:
   a rotatable gantry having an opening for receiving a subject to be scanned;
   an HF electromagnetic energy source configured to project a number of HF electromagnetic energy beams toward the subject;
   a generator configured to energize the HF electromagnetic energy source to at least a first energy state and a second energy state;
   a first filtering apparatus comprising a number of HF electromagnetic energy filters positional between the HF electromagnetic energy source and the subject, the number of HF electromagnetic energy filters including at least a first filter and a second filter wherein the first filter is positioned between the HF electromagnetic energy source and the subject by rotation of the first filtering apparatus before the HF electromagnetic energy source is energized to the first energy state and the second filter is positioned between the HF electromagnetic energy source and the subject by rotation of the first filtering apparatus before the HF electromagnetic energy source is energized to the second energy state; and
   wherein a plane of the first filter through which the HF electromagnetic energy beams pass when the source is energized to the first energy state is parallel with an axis of rotation of the first filtering apparatus, and a plane of the second filter through which the HF electromagnetic energy beams pass when the source is energized to the second energy state is parallel with the axis of rotation of the axis of rotation of the first filtering apparatus.

2. The CT system of claim 1 wherein the plane of the first filter is positioned orthogonal to the HF electromagnetic energy source when the HF electromagnetic energy source is energized to the first energy state, and the plane of the second filter is positioned orthogonal to the HF electromagnetic energy source when the energy source is energized to the second energy state.

3. The CT system of claim 1 wherein the HF electromagnetic energy source and the number of HF electromagnetic energy filters are rotatable about the subject.

4. The CT system of claim 1 further comprising:
a set of HF electromagnetic energy detectors configured to generate a set of electrical signals indicative of HF electromagnetic energy attenuated by the subject;
a DAS configured to receive the set of electrical signals; and
an image reconstructor connected to the DAS and configured to reconstruct an image of the subject from the electrical signals received by the DAS.

5. The CT system of claim 1 incorporated into a medical imaging device and wherein the subject is a medical patient.

6. The CT system of claim 1 wherein the movable table is configured to convey articles through the opening wherein the articles include pieces of luggage/baggage and packages.

7. The CT system of claim 6 incorporated into at least one of an airport inspection apparatus and a postal inspection apparatus.

8. The CT system of claim 1 further comprising a second filtering apparatus having a back surface, a first top surface, and a second top surface, wherein the two top surfaces are substantially co-planar and in a stepped relationship with one another, wherein a first filtration thickness is formed between the first top surface and the back surface, and a second filtration thickness is formed between the second top surface and the back surface, and wherein one of the first filtration thickness and the second filtration thickness is positioned between the HF electromagnetic energy source and the subject before the HF electromagnetic energy source is energized to either one of the first energy state and the second energy state.

9. The CT system of claim 1 wherein the first energy state is substantially equal to the second energy state.

10. A method of acquiring imaging data at more than one chromatic energy comprising the steps of:
projecting a first beam of electromagnetic energy from an x-ray source along a single projection path between the x-ray source and a detector and toward a subject to be scanned;
positioning a first filter of a first filtering apparatus in the single projection path before projection of the first beam;
projecting a second beam of electromagnetic energy from the x-ray source along the single projection path between the x-ray source and the detector and toward the subject; and
positioning a second filter of the first filtering apparatus in the single projection path before projection of the second beam, by rotation of the first filtering apparatus about an axis of rotation of the first filtering apparatus, wherein a plane of the first filter through which the first beam passes is parallel with the axis of rotation, and a plane of the second filter through which the second beam passes is parallel with the axis of rotation.

11. The method of claim 10 further comprising the steps of:
energizing an HF electromagnetic energy source to a first voltage to generate the first beam of electromagnetic energy;
rotating the first filtering apparatus about the axis of rotation to position the first filter along a path of rotation such that the first filter is in the projection path before energization of the HF electromagnetic energy source to the first voltage;
energizing the HF electromagnetic source to a second voltage to generate the second beam of electromagnetic energy; and
rotating the first filtering apparatus about the axis of rotation to position the second filter along the path of rotation such that the second filter is in the projection path before energization of the HF electromagnetic energy source to the second voltage.

12. The method of claim 10 wherein the step of rotating the first filtering apparatus further comprises positioning the plane of the first filter orthogonal to the single projection path during projection of the first beam of electromagnetic energy before the energy source is energized to the first voltage, and positioning the plane of the second filter orthogonal to the single projection path before projection of the second beam of electromagnetic energy when the energy source is energized to the second voltage.

13. The method of claim 10 further comprising the step of acquiring imaging data with the first beam of electromagnetic energy being substantially equal to the second beam of electromagnetic energy.

14. The method of claim 10 further comprising positioning a second filtering apparatus, the second filtering apparatus having a back surface, a first top surface, and a second top surface, wherein the two top surfaces are substantially co-planar and in a stepped relationship with one another, wherein a first filtration thickness is formed between the first top surface and the back surface, and a second filtration thickness is formed between the second top surface and the back surface, and wherein one of the first filtration thickness and the second filtration thickness is positioned between the HF electromagnetic energy source and the subject before projecting one of the first beam of electromagnetic energy and the second beam of electromagnetic energy.

15. A computer readable storage medium having a computer program stored thereon and representing a set of instructions that when executed by a computer causes the computer to:
energize an HF electromagnetic energy source to a first voltage to cause the HF electromagnetic energy source to project a first beam of electromagnetic energy toward a subject to be scanned;
position at least a first filter of a first filtering apparatus, between the HF electromagnetic energy source and the subject before energization of the HF electromagnetic energy source to the first voltage, wherein a plane of the first filter through which the first beam passes is parallel with an axis of rotation of the first filtering apparatus;
energize the HF electromagnetic energy source to a second voltage to cause the HF electromagnetic energy source to project a second beam of electromagnetic energy toward the subject; and
rotate the first filtering apparatus about the axis of rotation and position a second filter of the first filtering apparatus between the HF electromagnetic energy source and the subject before energization of the HF electromagnetic energy source to the second voltage, wherein a plane of the second filter through which the second beam passes is parallel with the axis of rotation of the first filtering apparatus.

16. The computer readable storage medium of claim 15 wherein the set of instructions further causes the computer to rotate the first filter and the second filter about the subject along a common path of rotation.

17. The computer readable storage medium of claim 15 wherein the set of instructions further causes the computer to rotate the first filter about the subject along a first path of rotation and rotate the second filter about the subject along a second path of rotation.

18. The computer readable storage medium of claim 15 incorporated into a medical imaging apparatus configured to acquire diagnostic imaging data of a medical patient.

19. The computer readable storage medium of claim 15 incorporated into a non-invasive parcel inspection apparatus including at least one of a postal inspection apparatus and a baggage inspection apparatus.

20. The computer readable storage medium of claim 15 wherein the set of instructions further causes positioning a second filtering apparatus, the second filtering apparatus having a back surface, a first top surface, and a second top surface, wherein the two top surfaces are substantially co-planar and in a stepped relationship with one another, wherein a first filtration thickness is formed between the first top surface and the back surface, and a second filtration thickness is formed between the second top surface and the back surface, and wherein one of the first filtration thickness and the second filtration thickness is positioned between the HF electromagnetic energy source and the subject before the HF electromagnetic energy source is energized to either one of the first voltage or the second voltage.

21. A filtering apparatus for a radiation emitting imaging system, the filtering apparatus comprising:
an axis of rotation;
a first filter connected to the filtering apparatus, the first filter having a first filtering power; and
a second filter connected to the filtering apparatus, the second filter having a second filtering power; and wherein a plane of the first filter through which radiation passes is parallel with the axis of rotation, and a plane of the second filter through which the radiation passes is parallel with the axis of rotation.

22. The filtering apparatus of claim 21 wherein a hub is configured to rotate the first filter about the axis of rotation into a path of HF electromagnetic energy before an HF electromagnetic energy source is energized to a first voltage, and rotate the second filter about the axis of rotation into the path of HF energy before the HF electromagnetic energy projection source is energized to a second voltage.

23. The filtering apparatus of claim 21 wherein the plane of the first filter is positioned orthogonal to the HF electromagnetic energy source when the energy source is energized to the first voltage, and the plane of the second filter is positioned orthogonal to the HF electromagnetic energy source when the energy source is energized to the second voltage.

24. The filtering apparatus of claim 21 wherein the hub is cylindrical or spherical, the filtering apparatus further comprising a third filter connected to the hub and a fourth filter connected to the hub, the first, the second, the third and the fourth filters having differing filtering powers and the third connection port being positioned 90° along the hub from the fourth connection port;
wherein the first, the second, the third, and the fourth filters are snap-fit, bolted, or integrated as a single integral body as attached to the hub.

25. The filtering apparatus of claim 21 further comprising an additional filtering apparatus, the additional filtering apparatus having a back surface, a first top surface, and a second top surface, wherein the two top surfaces are substantially co-planar and in a stepped relationship with one another, wherein a first filtration thickness is formed between the first top surface and the back surface, and a second filtration thickness is formed between the second top surface and the back surface, and wherein one of the first filtration thickness and the second filtration thickness is positioned between the HF electromagnetic energy source and the subject before the HF electromagnetic energy source is energized to either one of a first voltage or a second voltage.

* * * * *